United States Patent [19]

Ching et al.

[11] Patent Number: 5,072,013

[45] Date of Patent: Dec. 10, 1991

[54] SILYLATED OCTENYL ETHERS

[75] Inventors: Ta Y. Ching, Novato; Lon T. W. Lin, Vallejo, both of Calif.; Bert Gruber, Bedburg; Edgar Köeppelmann, Hilden, both of Fed. Rep. of Germany

[73] Assignee: Henkel Research Corporation, Santa Rosa, Calif.

[21] Appl. No.: 686,306

[22] Filed: Apr. 16, 1991

Related U.S. Application Data

[63] Continuation of Ser. No. 434,206, Nov. 13, 1989, abandoned.

[51] Int. Cl.$^5$ .............................. C07F 7/08; C07F 7/18
[52] U.S. Cl. ..................................... 556/442; 556/445; 428/409
[58] Field of Search ................. 556/442, 445; 428/409

[56] References Cited

U.S. PATENT DOCUMENTS

| | | | |
|---|---|---|---|
| 3,887,627 | 6/1975 | Romanelli | 260/63.2 R |
| 3,963,627 | 6/1976 | Cottrell | 252/4 |
| 4,124,556 | 11/1978 | Schafer et al. | 260/29.15 B |
| 4,483,973 | 11/1984 | Lucas et al. | 528/21 |

FOREIGN PATENT DOCUMENTS

| | | | |
|---|---|---|---|
| 1069057 | 1/1957 | Fed. Rep. of Germany | |
| 1796012 | 1/1972 | Fed. Rep. of Germany | |
| 781005 | 4/1980 | Japan | 556/445 U X |
| 0227536 | 9/1988 | Japan | 556/445 |
| 1248593 | 10/1971 | United Kingdom | 556/445 U X |

OTHER PUBLICATIONS

Advances in Organometallic Chemistry, vol. 17, pp. 141, 146-148, 152-157, 189-193 (1979).
Bulletin of the Chemical Society of Japan, vol. 41, pp. 454-460, Takahashi et al.
Tetrahedron, vol. 45, No. 2, Jan. 1989, A. Alexakis et al., pp. 381-389.

*Primary Examiner*—Paul F. Shaver
*Attorney, Agent, or Firm*—Ernest G. Szoke; Wayne C. Jaeschke; John E. Drach

[57] ABSTRACT

Silylated octenyl ethers are used to treat concrete to seal it against penetration by aqueous electrolyte solutions.

11 Claims, No Drawings

SILYLATED OCTENYL ETHERS

This application is a continuation, of application Ser. No. 07/434,206 filed on Nov. 13, 1989, now abandoned.

BACKGROUND OF THE INVENTION

1. Field of the invention

This invention relates to novel silylated octenyl ethers and their use as concrete sealers.

2. Description of the Related Art

Organosilicon compounds are extremely useful materials. Simple organosilicon compounds such as alkylsilanes have been used as additives in such things as paints, hydraulic fluids, heat transfer fluids, and dielectric fluids. Polymeric materials such as polysiloxanes have been used as defoamers, rubbers, coatings, and as additives in emulsions, greases, adhesives, and sealants. Most of these compounds contain silicon-oxygen and silicon-carbon bonds both of which contribute to the many unusual properties of these substances such as strong adhesion to smooth surfaces such as glass, thermal and oxidative stability, chemical inertness, resistance to weathering, and good dielectric strength. Because the presence of silicon-oxygen and carbon-silicon bonds contribute to the unique chemical and physical properties of organosilicon compounds, many methods of forming these types of bond have been developed over the years.

In the case of carbon-silicon bonds, one of the most widely used methods of forming them is through the addition of Si-H bonds to carbon-carbon multiple bonds. This reaction, which is called hydrosilation or hydrosilylation, is well known in the art and has been used to make many types organosilicon compounds. The reaction is usually carried out by reacting a substituted silane and a terminal alkene or terminal alkyne. These types of hydrosilylation reactions are normally initiated by heat, light, or radiation and catalyzed by peroxides, bases, and noble metal catalysts. The most widely used catalyst system is one involving chloroplatinic acid or some other platinum complex such as a platinum-olefin complex normally in a single phase system.

Japanese patent No. JP 7810005 discloses the product of the reaction of a trialkyl or trialkoxy silane with an octadienyl ester made by telomerizing butadiene and a carboxylic acid having from 2 to 11 carbon atoms in the presence of a Pd catalyst. These compounds are useful as silane coupling agents and provide high adhesion and compatibility with organic and inorganic materials. U.S. Pat. Nos. 4,483,973 and 4,528,353 disclose organosilicon compounds of the formula

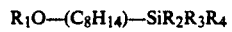

wherein $R^a$ and $R^b$ are $C_{1-8}$ monovalent hydrocarbon radicals, t varies from 0 to 3, and Z is a saturated, unsaturated or aromatic hydrocarbon radical, said radical being further functionalized by a member selected from the group consisting of amino, ether, epoxy, isocyanato, acryloxy, and acyloxy and mixtures thereof. U.S. Pat. No. 3,963,627 discloses compounds of the formula $R_n$-Si-$L_{4-n}$ wherein L is an alkoxyl group, R is a substituted hydrocarbon in which the hydrocarbon is an alkyl or alkenyl group, and the substituent may be an alkyl ether. U.S. Pat. No. 4,124,556 discloses a molding composition additive of the formula $(R'O)_3$—Si—R wherein R' is a hydrocarbon group and R is an alkyl group optionally substituted by an alkoxy group or other functionality.

SUMMARY OF THE INVENTION

One aspect of the present invention provides novel silylated octenyl ethers useful as coupling agents, emulsifiers and demulsifiers, textile processing aids, concrete sealers, and cosmetic additives. The present invention provides a composition of the formula 1

$$R_1O-(C_8H_{14})-SiR_2R_3R_4 \qquad 1$$

wherein the group $C_8H_{14}$ is a disubstituted octenyl moiety having a double bond at the 3, 4, 5, 6 or 7 position and an $R_1O$- substituent at the 1-position and an $-SiR^2R^3R^4$ substituent at either the 2— or the 8—position and wherein R1 is linear or branched alkyl or alkenyl group having from 1 to 22 carbon atoms, and each of $R_2$, $R_3$, and $R_4$ independently represents a linear or branched alkyl group having from 1 to 4 carbon atoms, an alkoxy group having from 1 to 4 carbon atoms, Cl, Br, or an acetoxy group. The present invention also provides compounds selected from the group consisting of a compound of the formula 2, 3, and 4

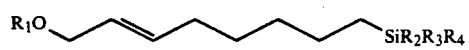

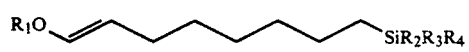

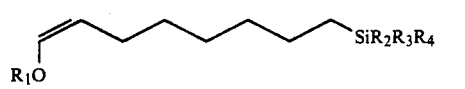

wherein $R_1$ is a linear or branched alkyl or alkenyl group having from 1 to 22 carbon atoms, and each of $R_2$, $R_3$, and $R_4$ independently represents a linear or branched alkyl group having from 1 to 4 carbon atoms, an alkoxy group having from 1 to 4 carbon atoms, Cl, Br, or an acetoxy group.

Another aspect of the present invention relates to a process for sealing concrete against penetration by an aqueous liquid comprising impregnating said concrete with an amount of a compound of the formula 1, 2, 3 or 4 or combinations thereof sufficient to limit the take-up of said liquid by said concrete to less than about 0.20 gm per square inch of concrete surface.

Still another aspect of the present invention relates to a composition comprising concrete and at least 0.01 grams per square inch of concrete surface of a compound of the formula 1, 2, 3 or 4 or combinations thereof.

DESCRIPTION OF THE PREFERRED EMBODIMENTS

The compounds of the present invention are silylated octenyl ethers of the formula 1, 2, 3 or 4 which can be made by silylating a 1-substituted 2,7-octadienyl ether (Formula 5)

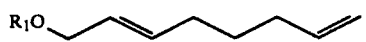

with a trisubstituted silane.

The octadienyl ethers that are used to make the compounds of the present invention can be made by the known method of reacting 1,3-butadiene with a linear or branched, alkyl or alkenyl alcohol in the presence of a transition metal catalyst such as platinum, palladium, or nickel catalyst. Methods of making the octadienyl ethers that can be used to make the compounds of the present invention are disclosed in U.S. Pat. No. 3,887,627; British Patent No. 1,248,593; Bulletin of the Chemical Society of Japan, 41, 254 (1968); Advances in Organometallic Chemistry, 17, 141 (1974).

Suitable silylating reagents are the $C_1$–$C_4$ alkoxysilanes, trimethoxysilane, triethoxysilane, tripropoxysilane, tri-isopropoxysilane, tributoxysilane, tri-(1-methyl-1-propoxy)silane, tri-(2-methyl-1-propoxy)silane, tri-(2-methyl-2-propoxy)silane, and mixed $C_1$–$C_4$ alkoxy silanes. "Mixed" $C_1$–$C_4$ alkoxy silanes are those in which one or more of the alkoxy groups are different from the other(s) as in dimethoxyethoxysilane and diethoxypropoxysilane and the like. Other suitable silylating reagents are triacetoxysilane, diacetoxymethoxysilane, acetoxydimethoxysilane, trichlorosilane, tribromosilane, linear or branched $C_1$–$C_4$ trialkyl silanes, dichloromethylsilane, and chlorodimethylsilane.

The reaction of a 1-substituted 2,7-octadienyl ether with a trisubstituted silane produces a number of derivatives of 8-silyl-1-alkoxy (or alkenoxy) octene as the major product and 2-silyl-1-alkoxy (or alkenoxy) octene as the minor product. For example, the major products of the reaction of triethoxysilane and 1-octoxy-2,7-octadiene in the presence of a catalyst are 8-triethoxysilyl-1-octoxy-cis-1-octene, 8-triethoxysilyl-1-octoxy-trans-1-octene, and 8-triethoxysilyl-1-octoxy-trans-2-octene. The composition of the product shows that the silylation takes place principally but not exclusively at the terminal double bond and that either the starting octadiene or the silylation product undergoes double bond isomerization. Analysis of the NMR spectrum of the product also shows about 65 mole % of an 8-silyl octene compound containing an —Si—$CH_2$—R group which is composed of 26% of a compound of formula 2, about 17% of a compound of formula 3, 10% of a compound of formula 4; and 22 % of a mixture of derivatives having a double bond at the 3, 4, 5, 6 or 7 position and the silyl group is at either the 2- or the 8-position. The mixture of 2- or 8-silyloctenyl ethers having a trans configuration about the double bond wherein the double bond is at the 3, 4, 5, 6 or 7 position is represented by formula 1.

In a preferred method of making the compounds of the present invention, approximately equimolar quantities of a trialkoxysilane and a 1-substituted 2,7-octadienyl ether (Formula 5) are mixed together in a toluene solution. To about one third of the toluene solution at 50° C. is added platinum divinyltetramethylsiloxane complex (about 1.3ml per mole of trialkoxysilane). The remainder of the toluene solution is added at such a rate as to keep the reaction temperature between 50° C. and 55° C. After the addition is finished, the reaction mixture is kept at between 50° C. and 55° C. until NMR analysis shows that the starting material has disappeared (about 4 hours). The reaction mixture is treated with decolorizing charcoal, and the product is isolated by stripping the reaction solvent to give about a 90% yield of product containing a mixture of compounds of the formula 1, 2 and 3.

In one group of preferred compounds of formula 1, $R_1$ is n-$C_8H_{17}$—, $R_2$, $R_3$, and $R_4$ are all equal to $OC_2H_5$, $OCH_3$, acetoxy, chloride or bromide.

In one group of preferred compounds of formula 2, $R_1$ is n-$C_8H_{17}$—, $R_2$, $R_3$, and $R_4$ are all equal to $OC_2H_5$, $OCH_3$, acetoxy, chloride or bromide.

In one group of preferred compounds of formula 3, $R_1$ is n-$C_8H_{17}$—, $R_2$, $R_3$, and $R_4$ are all equal to $OC_2H_5$, $OCH_3$, acetoxy, chloride or bromide.

In one group of preferred compounds of formula 4, $R_1$ is n-$C_8H_{17}$—, $R_2$, $R_3$, and $R_4$ are all equal to $OC_2H_5$, $OCH_3$, acetoxy, chloride or bromide.

Another aspect of the present invention relates to a process for sealing concrete against penetration by an aqueous liquid comprising impregnating said concrete with an amount of a compound of the formula 1, 2, 3 or 4 or combinations thereof sufficient to limit the take-up of said liquid by said concrete to less than about 0.20 gm per square inch of concrete surface. An aqueous liquid means water or an aqueous electrolyte solution. An aqueous electrolyte solution is any aqueous solution containing ions. Examples of aqueous electrolyte solutions include but are not limited to aqueous solutions of the water soluble salts of alkali metal and alkaline earth metals and transition metals such as NaCl, KCl, $CaCl_2$, $FeCl_3$ and the like. Impregnating the concrete means completely or partially infusing a compound of the present invention into the concrete. The impregnating step can be accomplished by any means which results in the penetration of the compound past the concrete surface and into the interior of the concrete such as by spraying the concrete with a solution of the compound, immersing the concrete into a solution of the compound, or applying a solution of the compound to the concrete surface so that the solvent will carry the compound into the interior of the concrete. It is intended that the concrete sealing process of the present invention be more than a surface treatment of the concrete. Preferably, the compounds of the present invention are applied to concrete so that they penetrate the concrete to a depth of from about 1 mm to about 5 mm below the concrete surface and thereby establish a an effective barrier against the penetration of aqueous liquids.

The amount of a compound of the formula 1, 2, 3 or 4 or combinations thereof sufficient to limit the take-up of an aqueous liquid by concrete to less than about 0.20 gm per square inch will vary depending upon the percent aqueous liquid take-up desired, the type of impregnating method and the nature of the concrete itself. At least about 0.01 grams of a compound of the formula 1, 2, 3 or 4 or combinations thereof per square inch of concrete surface is necessary to achieve a minimum resistance to penetration by an aqueous liquid. The exact amount for any particular application is easily determined by one skilled in the art. Still another aspect of the present invention relates to a composition comprising concrete having at least about 0.01 grams by weight of a compound of the formula 1, 2, 3 or 4 or combinations thereof per square inch of concrete surface.

The following examples will serve to illustrate but not limit the invention

EXAMPLE 1

Preparation of 1-octoxy-2-triethoxysilyloctene and 1-octoxy-8-triethoxysilyloctene.

Octyl octadienyl ether (100 g, 0.42 mole) and triethoxysilane (76 g, 0.47 mole) were mixed in 45 ml of toluene. One third of the solution was added to a three neck flask equipped with a condenser, a thermometer, and an addition funnel. The solution in the flask was heated to 50° C. and to this solution was added platinum divinyltetramethylsiloxane complex (0.6 ml). The remainder of the toluene solution is added at such a rate as to keep the reaction temperature between 50° C. and 55° C. After the addition was finished, the reaction mixture was kept at between 50° C. and 55° C. until NMR analysis shows that the starting material has disappeared (about 4 hours). The reaction mixture was treated with decolorizing charcoal, and the product (a colorless oil) was isolated by stripping the reaction solvent to give about a 90% yield of product containing a mixture of octoxysilanes in which the silyl group was at the 8- or 2-position (formula 1). Analysis by NMR did not detect any terminal double bond or Si-H bonds. NMR integration indicated 65 mole % of Si—CH$_2$—R, and 75 mole % of internal double bonds distributed relative to the ether oxygen as follows: 26% trans, alpha; 17 % cis, alpha; 10 % trans, beta; and 22 % trans, greater than beta to the ether oxygen.

EXAMPLE 2

Preparation of concrete blocks for treatment with 1-octoxy-2-triethoxysilyloctene and 1-octoxy-8-triethoxysilyloctene.

Ready-mix mortar was mixed 4:1 by volume with water and poured into 2" high, 2" i.d. cylindrical molds. After 3 days at ambient conditions, the blocks were carefully tapped from the molds with a cloth cushioned hammer and soaked in a saturated Ca(OH)$_2$ bath for 2 days. The blocks were then sanded with a belt sander to simulate aging. After a brief rinse to remove loose particles, the blocks were placed at room temperature in a forced air chamber. The blocks were dried for 2 days and then placed at ambient conditions for four additional days. The blocks were 11 days old at this point and weighed about 205g to about 215 grams.

EXAMPLE 3

Treatment of Concrete Blocks

A concrete block of example 2 was completely submerged in 40 grams of a 40% by weight isopropanol solution containing a compound to be tested as the sealant for a period of 30 minutes. After the block was removed from the solution, it was air dried overnight in a room temperature forced air chamber. The block was weighed before and after treatment to determine the weight gain.

EXAMPLE 4

Testing of Treated Concrete Blocks

A block treated as described in Example 3 was immersed in a 15% aqueous NaCl solution. The block was dried and weighed after 1 hr, 2 hrs, 4 hrs, and 8 hrs and then once a day for a total time period of 4 weeks. The relative weight gain of a block treated with a compound made according to Example 1, and that of a block treated with triethoxysilyloctane (C$_8$H$_{17}$Si(OEt)$_3$) relative to an untreated block is shown in Table 1. The data in table 1 show that a block treated with a compound of example 1 picks up 15.33% of the weight picked up by a non-treated (control) block while a block treated with C$_8$H$_{17}$Si(OEt)$_3$ picks up 20.85% of the weight picked up by a non-treated block. The 15.33% value corresponds to 0.17 gm of aqueous solution picked up per square inch of concrete surface area, and the 20.85% value corresponds to 0.22 gm per square inch.

TABLE 1

| Time (Days) | Weight Gain as % of Weight Gain of Control | |
|---|---|---|
| | Compound of Example 1 | C$_8$H$_{17}$Si(OEt)$_3$ |
| 1 | 5.4 | 5.6 |
| 2 | 6.4 | 8.4 |
| 3 | 6.6 | 12.8 |
| 4 | 7.6 | 14.2 |
| 5 | 7.7 | 15.9 |
| 6 | 8.3 | 16.8 |
| 7 | 8.9 | 16.7 |
| 14 | 13.2 | 17.8 |
| 21 | 14.0 | 19.8 |
| 28 | 15.3 | 20.8 |

What is claimed is:

1. A composition of the formula 1

$$R_1O\text{-}(C_8H_{14})\text{-}SiR_2R_3R_4 \qquad 1$$

wherein the group C$_8$H$_{14}$ is a disubstituted octenyl moiety having a double bond at the 3, 4, 5, 6 position and an R$_1$O-substituent at the 1-position and an —SiR$^2$R$^3$R$^4$ substituent at either the 2-or the 8-position and wherein R$_1$ is a linear or branched alkyl or alkenyl group having from 1 to 22 carbon atoms, and each of R$_2$, R$_3$, and R$_4$ independently represents a linear or branched alkyl group having from 1 to 4 carbon atoms, an alkoxy group having from 1 to 4 carbon atoms, Cl, Br, or an acetoxy group.

2. A compound selected from the group consisting of a compound of the formula 2, 3, and 4

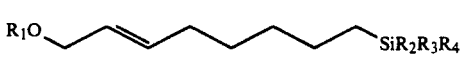
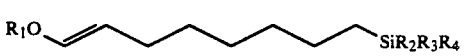
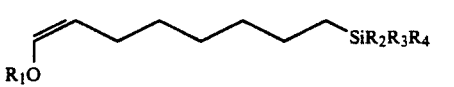

wherein R$_1$ is linear or branched alkyl or alkenyl group having from 1 to 22 carbon atoms, and each of R$_2$, R$_3$, and R$_4$ independently represents a linear or branched alkyl group having from 1 to 4 carbon atoms, an alkoxy group having from 1 to 4 carbon atoms, Cl, Br, or an acetoxy group.

3. A compound of claim 2 wherein in a compound of formula 2, 3 or 4 R$_1$ is 1-octyl and R$_2$, R$_3$, and R$_4$ are OC$_2$H$_5$.

4. A compound of claim 2 wherein in a compound of formula 2, 3 or 4 R$_1$ is 1-octyl and R$_2$, R$_3$, and R$_4$ are OCH$_3$.

5. A compound of claim 2 wherein in a compound of formula 2, 3 or 4 R$_1$ is 1-octyl and R$_2$, R$_3$, and R$_4$ are acetoxy.

6. A compound of claim 2 wherein in a compound of formula 2, 3 or 4 R$_1$ is 1-octyl and R$_2$, R$_3$, and R$_4$ are chloride or bromide.

7. A compound of claim 1 wherein in a compound of formula 1 $R_1$ is 1-octyl and $R_2$, $R_3$, and $R_4$ are $OC_2H_5$.

8. A compound of claim 1 wherein in a compound of formula 1 $R_1$ is 1-octyl and $R_2$, $R_3$, and $R_4$ are $OCH_3$.

9. A compound of claim 1 wherein in a compound of formula 1 $R_1$ is 1-octyl and $R_2$, $R_3$, and $R_4$ are acetoxy.

10. A compound of claim 1 wherein in a compound of formula 1 $R_1$ is octyl and $R_2$, $R_3$, and $R_4$ are chloride or bromide.

11. A composition comprising concrete and at least 0.01 grams per square inch of concrete surface of a compound of the formula 1, 2, 3 or 4 or combinations thereof

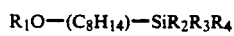

$R_1O-(C_8H_{14})-SiR_2R_3R_4$     1

2

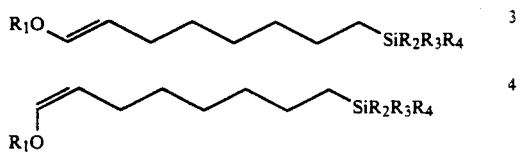

3

4 wherein the group $C_8H_{14}$ is a disubstituted octenyl moiety having a trans double bond is at the 3, 4, 5, 6 or 7 position and an $R_1O-$ substituent at the 1-position and an $-SiR^2R^3R^4$ substituent at either the 2- or the 8-position and wherein R1 is linear or branched alkyl or alkenyl group having from 1 to 22 carbon atoms, and each of $R_2$, $R_3$, and $R_4$ independently represents a linear or branched alkyl group having from 1 to 4 carbon atoms, an alkoxy group having to 4 carbon atoms, Cl, Br, or an acetoxy group.

* * * * *